(12) United States Patent
Niederberger et al.

(10) Patent No.: US 9,833,201 B2
(45) Date of Patent: Dec. 5, 2017

(54) MONITORING A PHYSIOLOGICAL PARAMETER OF A CYCLIST

(71) Applicant: THE BOARD OF TRUSTEES OF THE UNIVERSITY OF ILLINOIS, Urbana, IL (US)

(72) Inventors: Craig Niederberger, Chicago, IL (US); Peter Pfanner, Chicago, IL (US); James Hotaling, Chicago, IL (US); Matthew Clark, Chicago, IL (US); Andrew Graham, Chicago, IL (US); Michael Paradise, Chicago, IL (US); Michael Scott, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 14/767,346

(22) PCT Filed: Feb. 14, 2014

(86) PCT No.: PCT/US2014/016502
§ 371 (c)(1),
(2) Date: Aug. 12, 2015

(87) PCT Pub. No.: WO2014/127247
PCT Pub. Date: Aug. 21, 2014

(65) Prior Publication Data
US 2015/0374311 A1    Dec. 31, 2015

Related U.S. Application Data

(60) Provisional application No. 61/764,696, filed on Feb. 14, 2013.

(51) Int. Cl.
*A61B 5/00*   (2006.01)
*A61B 5/04*   (2006.01)
(Continued)

(52) U.S. Cl.
CPC ............ *A61B 5/748* (2013.01); *A61B 5/0022* (2013.01); *A61B 5/0205* (2013.01);
(Continued)

(58) Field of Classification Search
CPC ... A61B 5/746; A61B 5/4566; A61B 5/02028; A61B 5/4875; A61B 5/0205;
(Continued)

(56) References Cited

U.S. PATENT DOCUMENTS

| 6,272,936 B1 | 8/2001 | Oreper et al. |
| 2007/0021269 A1* | 1/2007 | Shum ...................... A61B 5/11 482/8 |

(Continued)

OTHER PUBLICATIONS

International Search Report and Written Opinion for Application No. PCT/US2014/016502 dated Jul. 8, 2014 (23 pages).

*Primary Examiner* — Gary Jackson
*Assistant Examiner* — Jessandra Hough
(74) *Attorney, Agent, or Firm* — Michael Best & Friedrich LLP

(57) ABSTRACT

The present invention is directed to a system for monitoring a physiological parameter of a cyclist, and methods of using the system. The system comprises a garment, a sensor, and a signal processor. The garment is configured to be worn by the cyclist. The sensor is fixedly coupled to the garment and configured to measure a signal representative of the physiological parameter during pedaling. The signal processor is operatively coupled to the sensor and configured to determine a diagnosis based on the measured signal. An alert is generated in response to the diagnosis substantially in real time.

17 Claims, 8 Drawing Sheets

(51) Int. Cl.
*A61B 5/02* (2006.01)
*A61B 5/0205* (2006.01)
*A61B 5/22* (2006.01)
*A61B 5/0245* (2006.01)
*A61B 5/053* (2006.01)
*A61B 5/11* (2006.01)
*A61B 5/145* (2006.01)
*A61B 5/024* (2006.01)
*A61B 5/08* (2006.01)
*A61B 5/091* (2006.01)

(52) U.S. Cl.
CPC ............ *A61B 5/02028* (2013.01); *A61B 5/04* (2013.01); *A61B 5/221* (2013.01); *A61B 5/4519* (2013.01); *A61B 5/4566* (2013.01); *A61B 5/4875* (2013.01); *A61B 5/6804* (2013.01); *A61B 5/6806* (2013.01); *A61B 5/6807* (2013.01); *A61B 5/6823* (2013.01); *A61B 5/6824* (2013.01); *A61B 5/6825* (2013.01); *A61B 5/6828* (2013.01); *A61B 5/7246* (2013.01); *A61B 5/7278* (2013.01); *A61B 5/7445* (2013.01); *A61B 5/02438* (2013.01); *A61B 5/02455* (2013.01); *A61B 5/0537* (2013.01); *A61B 5/0816* (2013.01); *A61B 5/091* (2013.01); *A61B 5/1116* (2013.01); *A61B 5/14517* (2013.01); *A61B 2503/10* (2013.01)

(58) Field of Classification Search
CPC ... A61B 5/6807; A61B 5/0022; A61B 5/6806; A61B 5/221; A61B 5/7445; A61B 5/4519; A61B 5/091; A61B 5/0816; A61B 2503/10; A61B 5/02438; A61B 5/7275
See application file for complete search history.

(56) References Cited

U.S. PATENT DOCUMENTS

| | | | |
|---|---|---|---|
| 2008/0269644 A1* | 10/2008 | Ray | A61B 5/224 600/587 |
| 2010/0198453 A1* | 8/2010 | Dorogusker | A63B 24/0062 701/31.4 |
| 2010/0211355 A1* | 8/2010 | Horst | A61B 5/1038 702/173 |
| 2010/0292615 A1* | 11/2010 | Niederberger | A61B 5/103 600/587 |
| 2010/0298899 A1* | 11/2010 | Donnelly | A61B 5/02055 607/6 |
| 2012/0197353 A1 | 8/2012 | Donnelly et al. | |
| 2012/0229270 A1* | 9/2012 | Morley | A61B 5/6806 340/539.12 |

* cited by examiner

| PERSONAL | BIKE | ENVIRONMENT | NETWORK |
|---|---|---|---|
| ARTERIAL OCCLUSION: PELVIS, HANDS, FEET | SEAT HEIGHT | TEMPERATURE | TEAM COMPUTER SYNC |
| LUNG CAPACITY | SEAT ANGLE | HUMIDITY | COACH: LIVE ANALYSIS |
| WEIGHT | TIRE PRESSURE | AIR PRESSURE | BIKE TEAMS |
| WATTAGE | HANDLEBAR PLACEMENT | BANK / CAMBER | GROUP RIDES |
| SPEED VS. WATTS | STAND UP / BIKE SHIFTS | SITUATION AWARENESS: CARS, POTHOLES, ETC. | KEEP RIDERS TOGETHER |
| SPINE ALIGNMENT | PUSHING VS. PULLING | DRAFTING / CROSS-WHEELING | AVERAGE WATTAGE |
| HEART RATE | ARDUINO LIVE ANALYSIS | TRAFFIC SIGNALS | TEAM POSITIONING |
| POSTURE | PRESSURE: SUSTAINED VS. IMPACT | DANGEROUS INTERSECTIONS | |
| PERSPIRATION RATE | SHIFTING / SEAT HEIGHT SYSTEM CONTROL | RACE / TRACK "HISTORY" | |
| pH | CORNERING / CANTILEVER | | |
| OXYGEN SATURATION et. $CO_2$ | | | |
| MUSCLE GROUPS | | | |
| HYDRATION | | | |

*FIG. 10*

MONITORING A PHYSIOLOGICAL PARAMETER OF A CYCLIST

CROSS-REFERENCE TO RELATED APPLICATIONS

This is a U.S. national stage entry of International Patent Application No. PCT/US2014/016502, filed on Feb. 14, 2014, which claims priority to U.S. Provisional Patent Application No. 61/764,696, filed on Feb. 14, 2013, the entire contents of all of which are fully incorporated herein by reference.

FIELD OF THE INVENTION

This invention relates generally to monitoring a physiological parameter during sports. More particularly, this invention relates to monitoring a physiological parameter during bicycle riding.

BACKGROUND OF THE INVENTION

During prolonged bicycle riding, for example during long distance rides or trail cycling, bicyclists commonly experience discomfort or sensory and motor impairment. Symptoms of the discomfort or impairment may include a genital numbness and/or paresthesia in the cyclist's forearms, hands, fingers, and feet. These symptoms may persist anywhere from several days to months, and may potentially result in erectile dysfunction and long-term nerve damage. One reason for these symptoms is the fact that a cyclist engages the bicycle seat, handlebar, and the pedals during bicycle riding, and exerts significant pressure or force on these portions of the bicycle. In turn, the force that the cyclist exerts on the portions of the bicycle is matched by a corresponding force exerted by these portions on the cyclist. When the corresponding force is concentrated on particular regions of the cyclist, discomfort or impairment may occur, which may adversely affect the performance of the cyclist. Thus, there has developed a need to mitigate discomfort or sensory and motor impairment during prolonged bicycle riding to improve the performance of the cyclist.

SUMMARY OF THE INVENTION

The inventors have discovered that discomfort or sensory and motor impairment can be mitigated during prolonged bicycle riding by monitoring a physiological parameter with a sensor fixedly coupled to a garment worn by the cyclist.

Accordingly, in an embodiment, this invention is a system for monitoring a physiological parameter of a cyclist, comprising a garment, a sensor, and a signal processor. The garment is configured to be worn by the cyclist. The sensor is fixedly coupled to the garment and configured to measure a signal representative of the physiological parameter during pedaling. The signal processor is operatively coupled to the sensor and configured to determine a diagnosis based on the measured signal. An alert is generated in response to the diagnosis substantially in real time.

In another embodiment, this invention is a method of monitoring a physiological parameter of a cyclist, comprising measuring a signal representative of the physiological parameter during pedaling. The measured signal is processed with a signal processor to determine a diagnosis. An alert is generated in response to the diagnosis substantially in real time.

Other aspects of the invention will become apparent by consideration of the detailed description and accompanying drawings.

BRIEF DESCRIPTION OF THE FIGURES

FIG. 10. Schematic illustration of a system according to an alternate embodiment of the invention, including a sensor, a signal processor, and a display device.

DETAILED DESCRIPTION

Figure 1:
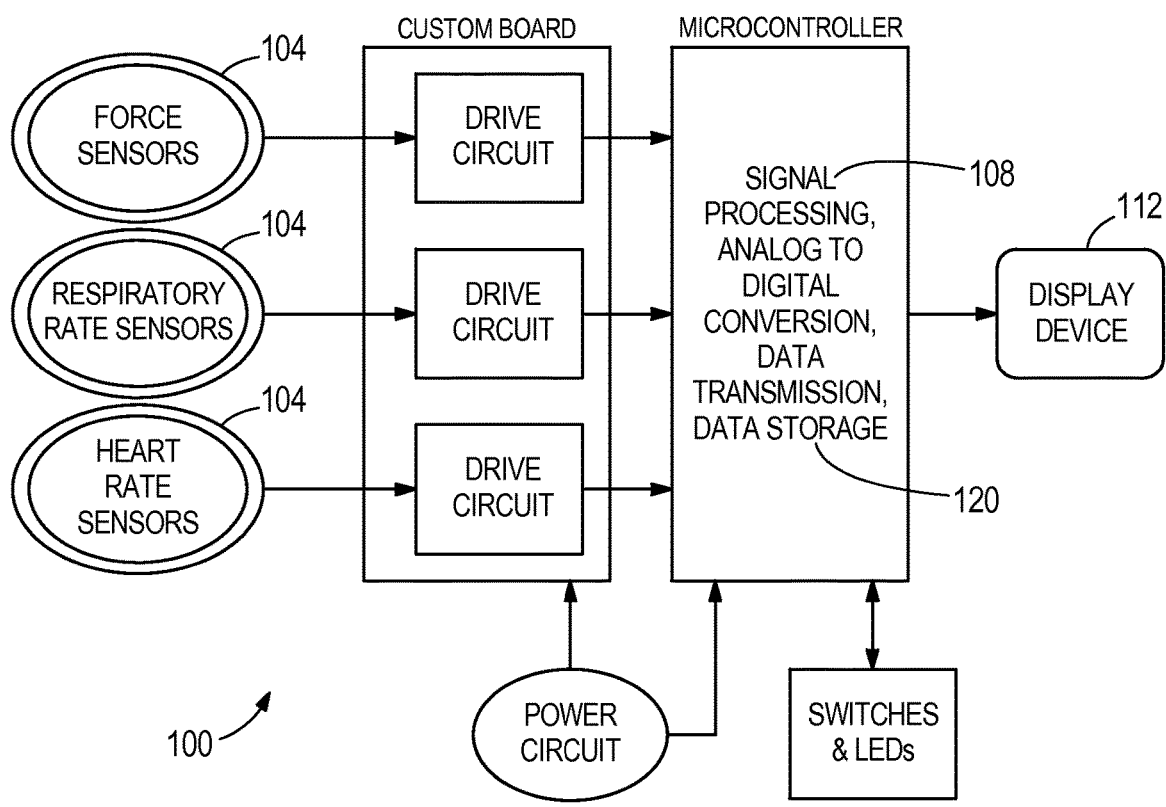
FIG. 1. Schematic illustration of a system according to one embodiment of the invention, including a sensor, a signal processor, and a display device.

Described herein is a system for monitoring a physiological parameter of a cyclist, and methods of using the system. The system comprises a garment, a sensor, and a signal processor. The garment includes a fabric defining an inner surface contacting the cyclist when the garment is worn by the cyclist, and an outer surface opposite the inner surface. The sensor is fixedly coupled to the inner surface and configured to measure a signal representative of the physiological parameter during pedaling. The signal processor is operatively coupled to the sensor and configured to determine a diagnosis based on the measured signal. An alert is generated in response to the diagnosis substantially in real time.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "operatively coupled," "operably coupled," or "operably connected" refers to a configuration of elements such as device components, wherein an action or reaction of one element affects another element, but in a manner that preserves each element's functionality. Operatively coupled device components may be in contact, such as in electrical contact by a signal-conducting wire between a sensor and a microcontroller containing a microprocessor. Alternatively, operatively coupled components may be coupled by one or more intervening components. In another alternative, operatively coupled components may not be physically coupled, but may be wirelessly coupled such that a signal is output from one component and wirelessly received by a second component.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising," "consisting essentially of" and "consisting of" may be replaced with either of the other two terms. The invention illustratively described herein suitably may be practiced in the absence of any element or elements, limitation or limitations which is not specifically disclosed herein.

As used herein, "perineum region" refers to an area between the pubic symphysis and the coccyx and is used to refer to both the surface region and underlying structure such as blood vessels, including blood vessels that supply blood to the penis in males. In particular, it is that region that is generally supported by a conventional bicycle seat.

As used herein, "perineal artery occlusion pressure" or "perineal artery occlusion force" refers to the pressure or force at which blood flow in the artery stops. For example, perineal artery occlusion force could be about 10 N on each of the right and left branch of perineal artery depending on the subject.

2. System for Monitoring a Physiological Parameter of a Cyclist

Turning now to the drawings, FIG. 1 shows a system 100 according to one embodiment of the invention, including a plurality of sensors or personal sensors 104, a signal processor 108, and a display device 112. The system 100 may be used by a cyclist C (not shown in FIG. 1; see FIGS. 2-6) during riding a bicycle B (not shown in FIG. 1; see FIG. 5), which may be a regular bicycle such as racing bike, road bike, mountain bike or a hybrid. Alternatively, the system 100 may be used in relation to bike fitting or testing with a stationary or simulated bicycle, or even simply a post optionally having pedals to support the user's feet.

In the illustrated embodiment, the sensors 104 include force sensors, respiratory rate sensors, and heart rate sensors. As explained below, each sensor 104 is coupled to a garment 116 (not shown in FIG. 1; see FIGS. 2-6) and configured to measure a signal representative of a physiological parameter during pedaling. In some embodiments, the sensors 104 may be configured to measure signals representative of physiological parameters comprising at least one of arterial occlusion force, lung capacity, weight, wattage output, spine alignment, posture, respiratory rate, perspiration rate, heart rate, muscle group use, and hydration. In other embodiments, the sensors 104 may be configured to measure signals representative of other physiological parameters. Any force or pressure sensor known in the art may be used so long as the sensor is capable of reliably measuring a signal representative of a physiological parameter during the bicycle exercise. The sensors 104 may measure pedaling cadence, example. In some embodiments, force is measured and reported, while in other embodiments, pressure is calculated by the formula $P=F/A$, where P is pressure, F is force, and A is the area (e.g., area of a sensor over which the force F is applied). One example of a suitable sensor is a Flexiforce® force sensor from Tekscan (South Boston, Mass.) (see, e.g., U.S. Pat. No. 6,272,936). Any sensor, however, that is thin so as to provide non-intrusive measurement and capable of reliable positioning to the garment 116 may be used. The sensor may be re-positioned on the garment so as to appropriately measure the desired physiological parameter. This re-positioning may be accomplished via adjustable straps, for example, that move the sensors to a desired location on the garment. Upon re-positioning, the sensors may be fixedly coupled to the garment. In an aspect, the sensor 104 measures the force over area that is circular having a diameter that is less than or equal to 1 cm, 0.8 cm, 0.5 cm or about 0.95 cm.

Although FIG. 1 illustrates the system 100 as including three types of sensors 104, other embodiments may utilize other types or numbers of sensors 104. The system 100 and methods disclosed herein can use any number of sensors 104 as desired. However, as the number of sensors 104 increases, redundant and unnecessary measurements may be obtained. Accordingly, in an aspect, the number of sensors 104 may be no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1.

In some embodiments, each sensor 104 may be configured to measure a respective signal at predetermined intervals. In an aspect, the data acquisition frequency may be about 20 Hz, from about 10 Hz to about 30 Hz, or selected based on the cadence of the rider, so that data acquisition occurs at least twice during the range of pedal motion. Under different ride conditions and users, cadence may range from 50 rpm to about 120 rpm. In an aspect, the acquisition may be periodically turned on and then turned off to ensure data is sampled over the entire ride.

In some embodiments, a data storage 120 may be operatively coupled to the sensor 104 and configured to record the measured signal. The data storage 120 may be used to store the measured signal locally or to a remote location, for storage and later analysis. In some embodiments, the data storage 120 may include an SD card, a MicroSD card, and a universal serial bus (USB) device. In other embodiments, however, the system 100 may not include the data storage 120.

The signal processor 108 is operatively coupled to the sensors 104, and configured to determine a diagnosis based on the measured signal. In some embodiments, the signal processor 108 may include a self-contained microcontroller (and associated components such as power supply, pressure sensors, wiring) capable of being used in the field, such as during a non-stationary bicycle ride outdoors. In contrast, a microcontroller that is not self-contained may not be portable for real-time use and remain in the testing facility where it is hooked into a computer or other data-recording/observing device. In some embodiments, the signal processor 108 may include a Rabbit® 4000 microprocessor that receives analog input from the sensors 104 and converts them into digital signals to be stored in its memory. Other optional components may be included in the microcontroller as desired, including switches and LED to indicate sensor and/or recording status. For example, operational amplifiers may be included such as National Semiconductor LM324 low power quad operational simplifiers.

In some embodiments, the system 100 includes a signal transmission network operatively coupled to the sensors 104 and signal processor 108. The signal transmission network may be configured to transmit the signal according to at least one of a wired interface and ANT+, Bluetooth, ZigBee, WiFi, cellular access technologies (e.g., 2G, 3G, Universal mobile Telecommunications Systems (UMTS), GSM, Long Term Evolution (LTE), or more), etc.

Figure 2:
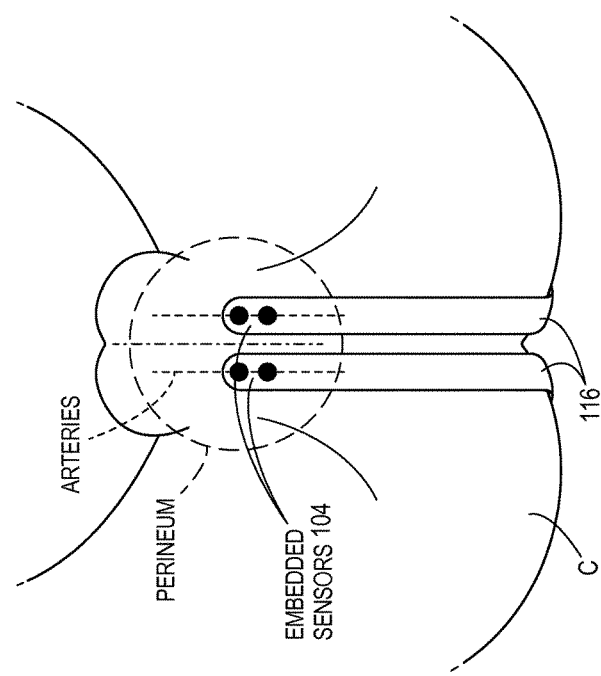
FIG. 2. Plane view of the sensor of FIG. 1 contacting a perineum region of a cyclist.

Referring also to FIG. 2, the system 100 includes the garment 116 (e.g., trouser including strips for embedding the sensors 104) configured to be worn by the cyclist C. The illustrated sensors 104 are fixedly coupled to the garment 116. In the illustrated embodiment, the sensors 104 are sewn or stitched to the garment 116 and substantially surrounded thereby or embedded therein. In other embodiments, however, the sensor 104 may be fixedly coupled to the garment 116 via other suitable mechanisms. For example, the sensor 104 may be fixedly coupled to the garment 116 by adhesive tape, a bandage, or any fabric hook and loop fastener, such as a Velcro fastener. The sensors 104 may be pressure sensors, such as a pressure transducer whose voltage output is related to the force exerted on a force-sensing element such as a resistor whose resistance changes depending on the applied force.

In the illustrated embodiment, the sensors 104 are fixedly coupled to a crotch portion of the garment 116, positioned adjacent a perineum region of the cyclist C when the garment 116 is worn by the cyclist C. The illustrated sensors 104 are configured to measure a signal representative of the perineal arterial occlusion pressure or force. In the illustrated embodiment, four sensors 104 are fixedly coupled to the crotch portion of the garment 116, at distal and proximal positions of the left and right internal pudendal arteries respectively. In other embodiments, six sensors 104 may be fixedly coupled to the crotch portion of the garment 116, at distal, mid, and proximal positions of the left and right internal pudendal arteries. In still other embodiments, other numbers of sensors 104 may be fixedly coupled to the crotch portion of the garment 116 so as to suitably monitor a dynamic pressure or force adjacent a desired location while the cyclist C is pedaling or moving.

In an embodiment, the signal processor 108 determines a diagnosis based on the measured perineal arterial pressure or force and a user-selected perineal arterial occlusion pressure or force level. In an aspect, the user-selected occlusion pressure or force level is the perineal arterial occlusion pressure, force, or a fraction thereof, such as greater than or equal to 80%, greater than or equal to 90%, or selected from a range that is greater than or equal to 80% and less than or equal to 100% of the perineal arterial occlusion pressure or force.

Figure 3:
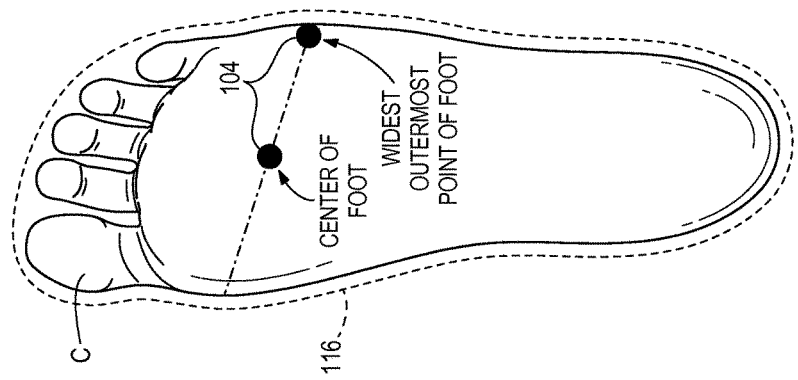
FIG. 3. Plane view of the sensor of FIG. 1 contacting a foot of a cyclist.

Referring also to FIG. 3, the illustrated sensors 104 are fixedly coupled to a sole portion of the garment 116 (e.g., shoe), positioned adjacent a foot of the cyclist C. In the illustrated embodiment, the sensors 104 are positioned adjacent a center of the foot and an outermost point of the foot when the garment 116 is worn by the cyclist C. In other embodiments, the sensors 104 may be fixedly coupled to the garment 116 so as to suitably monitor a dynamic pressure or force adjacent the toes, forefoot, instep, arch, or heel of the cyclist C while the cyclist C is moving. In still other embodiments, the sensors 104 may be configured to measure a signal representative of the weight of the cyclist C when the garment 116 is worn by the cyclist C.

Figure 4:
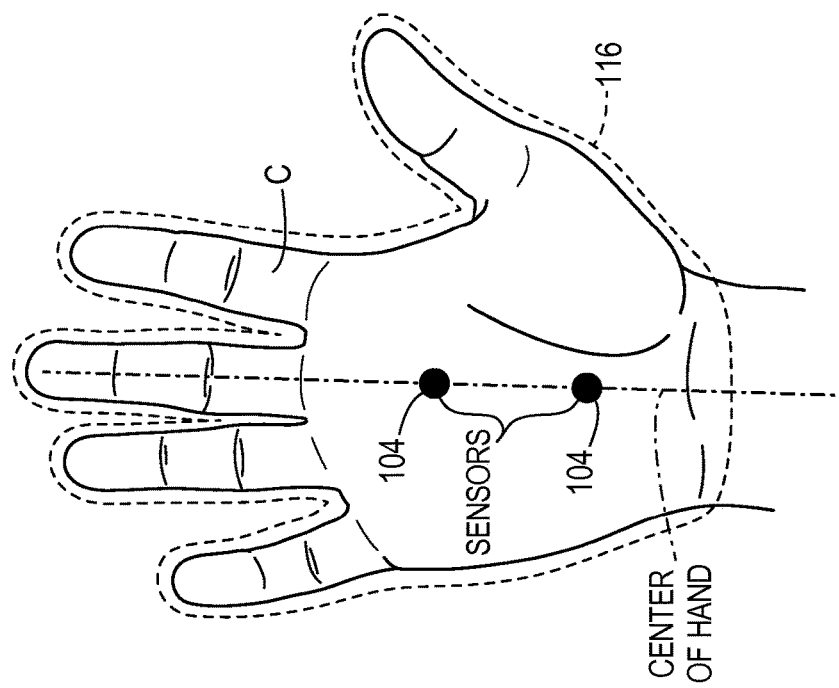
FIG. 4. Plane view of the sensor of FIG. 1 contacting a hand of a cyclist.

Referring also to FIG. 4, the illustrated sensors 104 are fixedly coupled to a palm portion of the garment 116 (e.g., glove), positioned adjacent a hand of the cyclist C when the garment 116 is worn by the cyclist C. In the illustrated embodiment, the sensors 104 are positioned adjacent a centerline of the hand when the garment 116 is worn by the cyclist C. In other embodiments, the sensors 104 may be positioned adjacent a radial artery or any other peripheral arteries in the hand of the cyclist C. In further embodiments, the sensors 104 may be fixedly coupled to the garment 116 so as to suitably monitor a dynamic pressure or force adjacent the hypothenar eminence, ulnar nerve, or palmar metacarpal arteries of the cyclist C while the cyclist C is pedaling or moving. In still other embodiments, the sensors 104 may be configured to measure a signal representative of oxygen saturation and positioned adjacent a fingertip of the cyclist C when the garment 116 is worn by the cyclist C.

Figure 5:
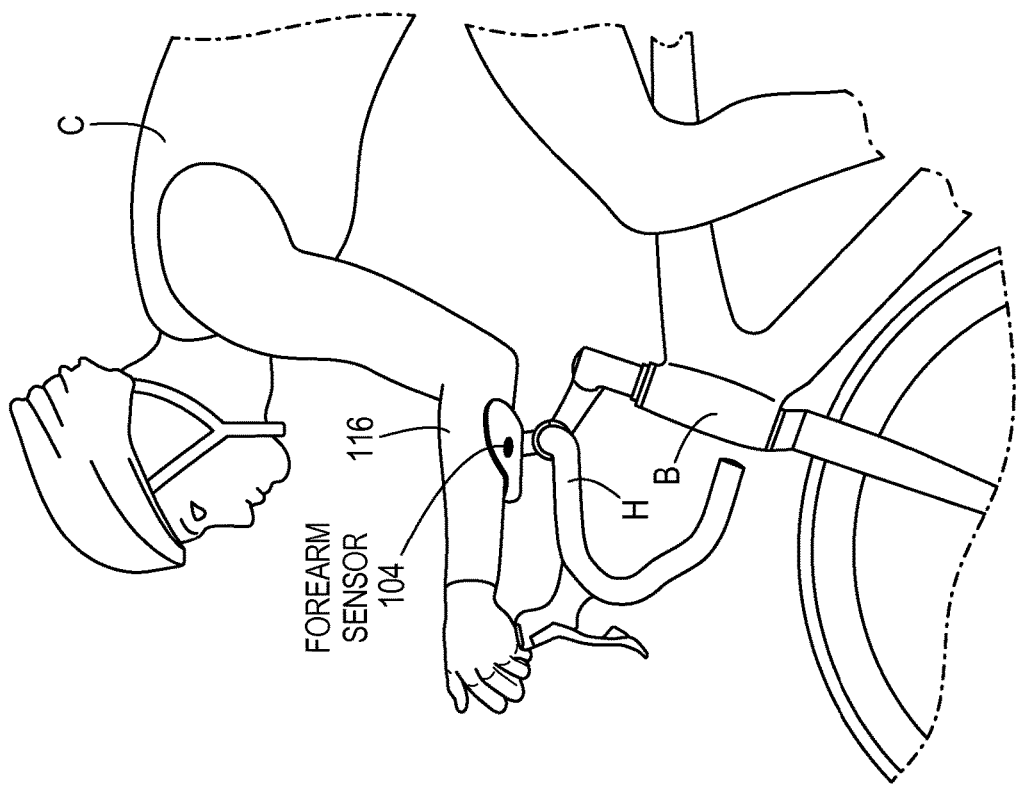
FIG. 5. Side view of the sensor of FIG. 1 contacting a forearm of a cyclist.

Referring also to FIG. 5, the illustrated sensor 104 is fixedly coupled to a forearm portion of the garment 116, positioned adjacent a forearm F of the cyclist C when the garment 116 is worn by the cyclist C. In other embodiments, the sensors 104 may be fixedly coupled to the garment 116 so as to suitably monitor a dynamic pressure or force adjacent the radial artery, an ulnar artery, or any other peripheral arteries in the forearm of the cyclist C while the cyclist C is pedaling or moving.

Figure 6:
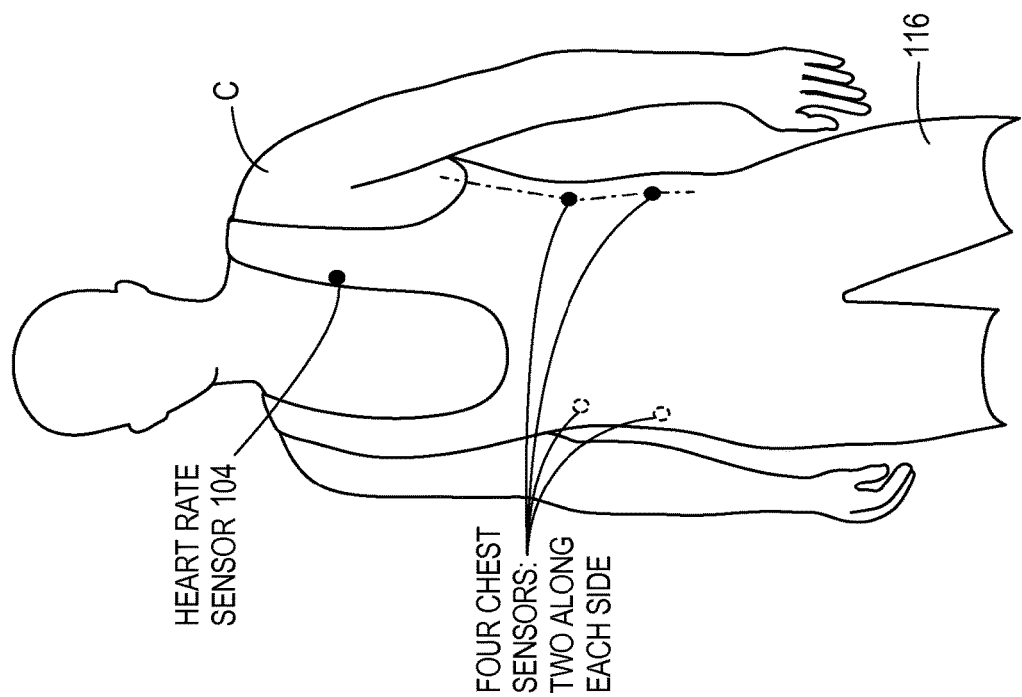
FIG. 6. Perspective view of the sensor of FIG. 1 contacting a torso of a cyclist.

Referring also to FIG. 6, the illustrated sensors 104 are fixedly coupled to a torso of the garment 116 (e.g. bib). In the illustrated embodiment, one sensor 104 is positioned adjacent a chest portion and four sensors 104 are positioned adjacent side rib portions of the cyclist C (two sensors 104 along each side). In other embodiments, other numbers of sensors 104 may be fixedly coupled to the torso of the garment 116 so as to suitably monitor a physiological parameter such as heart rate, respiratory rate, and lung capacity while the cyclist C is moving. In some embodiments, the garment 116 may include a fabric that stretches and recovers or resiliently returns from stretch in response to motion of the cyclist C. The sensors 104 in this embodiment may include a strain gauge configured to measure the chest wall movement. In other embodiments, the sensors 104 may include a piezoelectric compression sensor or any other mechanical or electric sensors depending on the use requirements or preferences for the system 100. Moreover, although the illustrated embodiment includes a plurality of sensors 104, other embodiments may include a single sensor 104.

Figure 7:
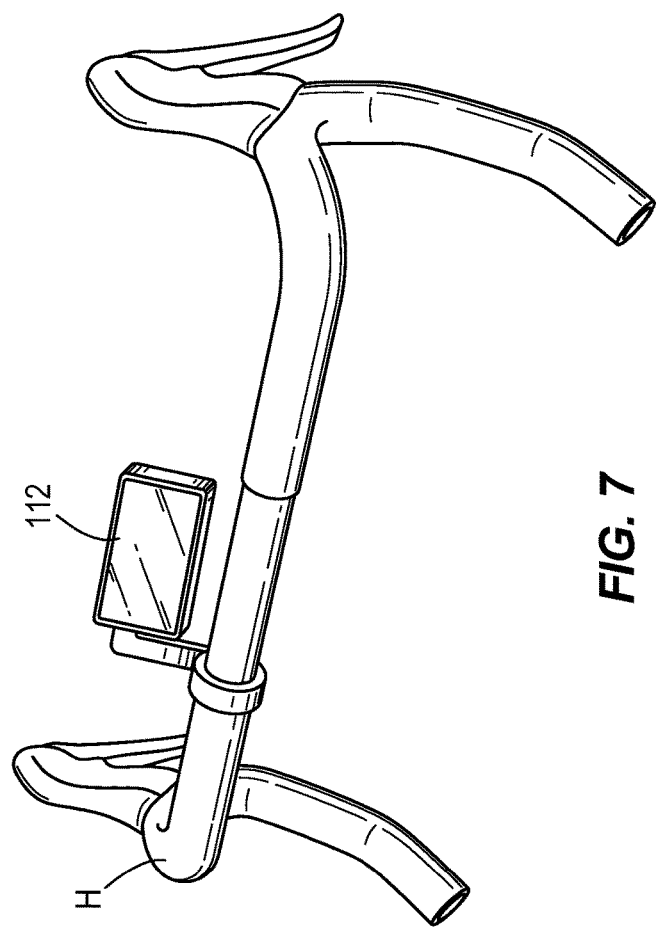
FIG. 7. Perspective view of the display device of FIG. 1 coupled to a handlebar of a bicycle.
Figure 8:
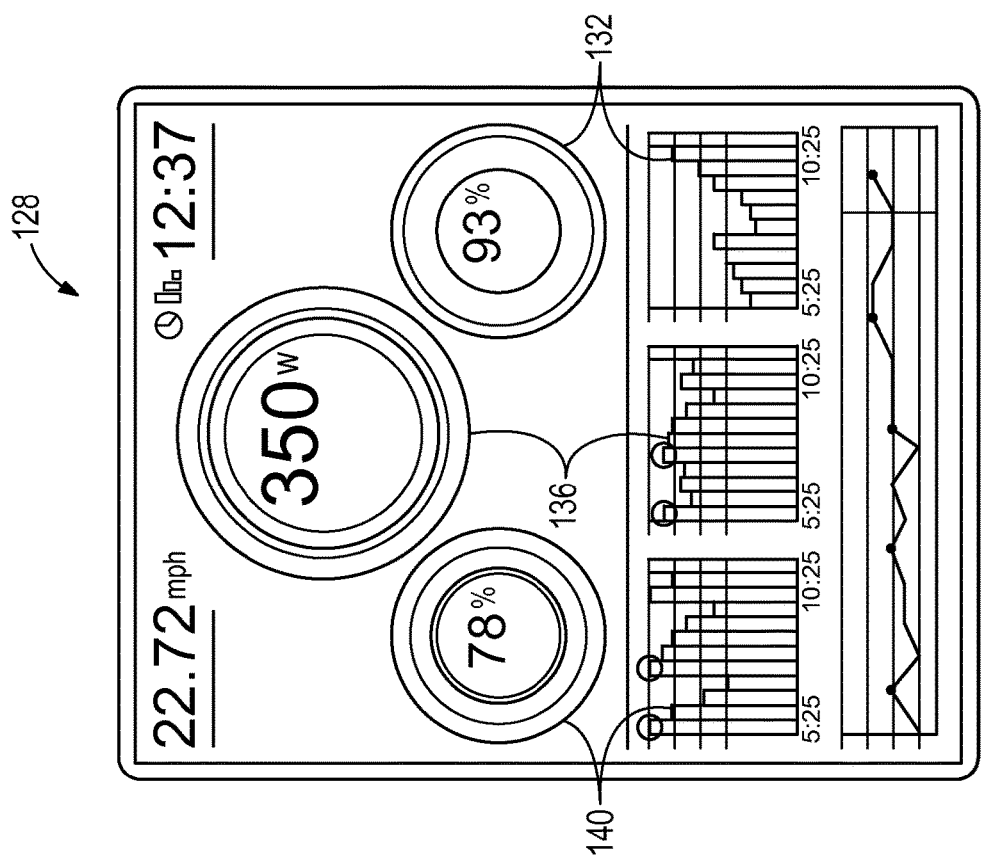
FIG. 8. Plane view of the display device of FIG. 1, illustrating a diagnostics display.

Referring also to FIG. 7, the system 100 may include the display device 112 coupled to a handlebar H of the bicycle B (not shown; see FIG. 5). Also referring to FIGS. 8 and 9, the display device 112 may be operatively coupled to the signal processor 108 and configured to generate a diagnostics display 128 in response to the diagnosis substantially in real time. In the illustrated embodiment, the diagnostics display 128 comprises a listing of arterial pressure or force 132, wattage output 136, and hydration 140. In other embodiments, the diagnostics display 128 may further comprise a listing of at least one of lung capacity, weight, spine alignment, posture, respiratory rate, perspiration rate, heart rate, and muscle group use. In still other embodiments, the diagnostics display 128 may further comprise a listing of other physiological parameters.

Figure 9:
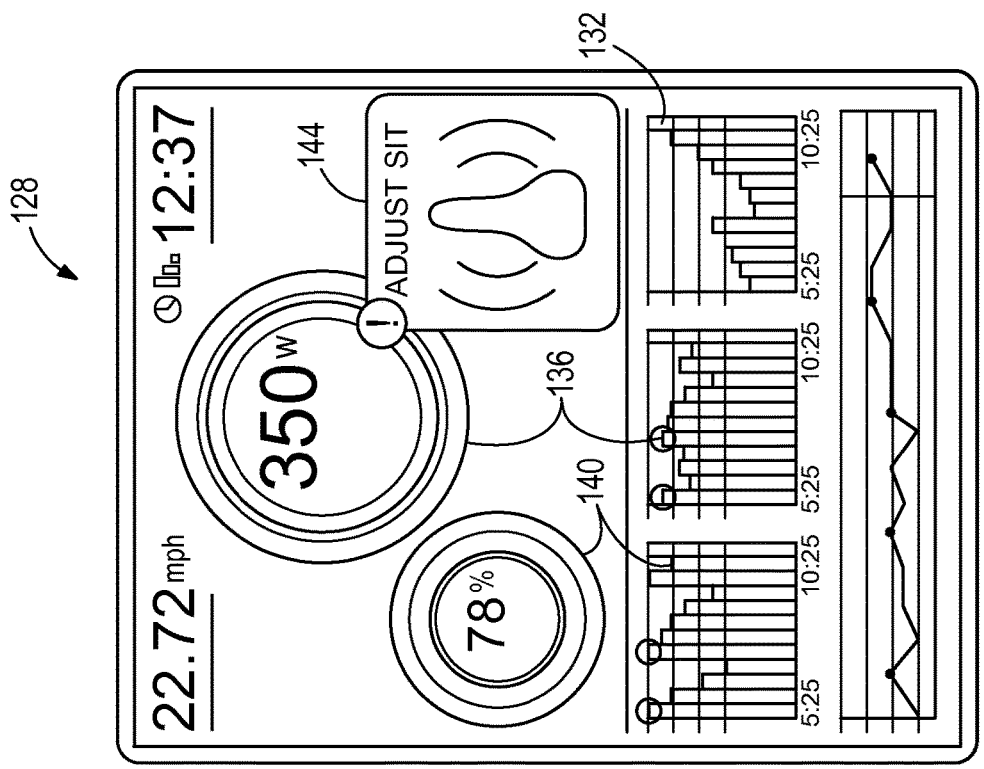
FIG. 9. Plane view similar to FIG. 8, illustrating the display device generating an alert.

Referring also to FIG. 9, the display device 112 may generate an alert, alarm, or warning 144 substantially in real time in response to the diagnosis of the signal processor 108. For example, when the signal processor 108 determines that the measured perineal arterial pressure or force meets or exceeds a fraction of the user-selected perineal arterial occlusion pressure or force level, the display device 112 may display the illustrated alert 144. The display device 112 can thus provide a real-time warning so as to preempt potentially deleterious effects on the performance of the cyclist C. The actual cut-off values for generating the alert 144 may be assigned depending on the degree of risk tolerance in the particular setting.

FIG. 10 shows a system 200 according to an alternate embodiment of the invention. Like parts are identified using like reference numerals. In addition to the personal sensors 104, the system 200 in this embodiment includes environmental sensors 204. The environmental sensors 204 may be configured to measure signals representative of temperature, humidity, air pressure, bank/camber of the bicycle B, situation awareness (e.g., cars, potholes, etc.), drafting/cross-wheeling of the bicycle B, traffic signals, dangerous intersections, and race/track history. The signal processor 108 is operatively coupled to the personal sensors 104 and the environmental sensors 204, and configured to determine a diagnosis based on the measured signals.

An alert, alarm, or warning is generated substantially in real time in response to the diagnosis of the signal processor 108. The alert may be in the form of automatically adjusting portions of the bicycle B. In some embodiments, the one or more of the following may be automatically adjusted substantially in real time in response to the diagnosis of the signal processor 108: seat height, seat angle, tire pressure, and handlebar placement. In other embodiments, gears of the bicycle B may be shifted in response to the diagnosis of the signal processor 108. Alternatively, the alert may prompt the user to manually adjust portions of the bicycle. The alert may preempt potentially deleterious effects on the performance of the cyclist C. In some embodiments, the one or more of the following may be manually adjusted in response to the diagnosis of the signal processor 108: seat height, seat angle, tire pressure, and handlebar placement. In other embodiments, gears of the bicycle B may be manually shifted in response to the diagnosis of the signal processor 108.

Figure 11:
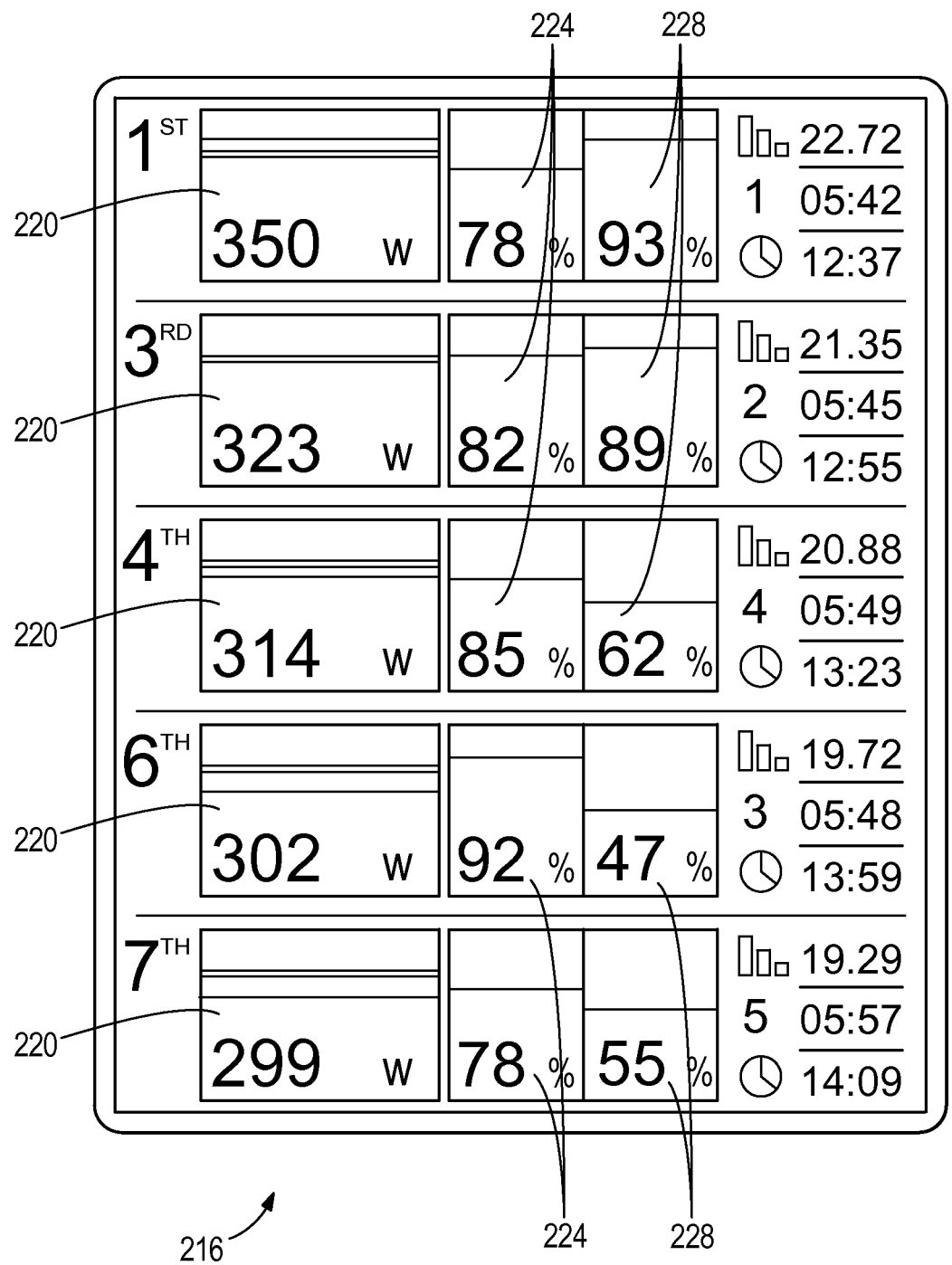
FIG. 11. Plane view of the display device of FIG. 10, illustrating a diagnostics display in comparison with a network of cyclists.
Figure 12:
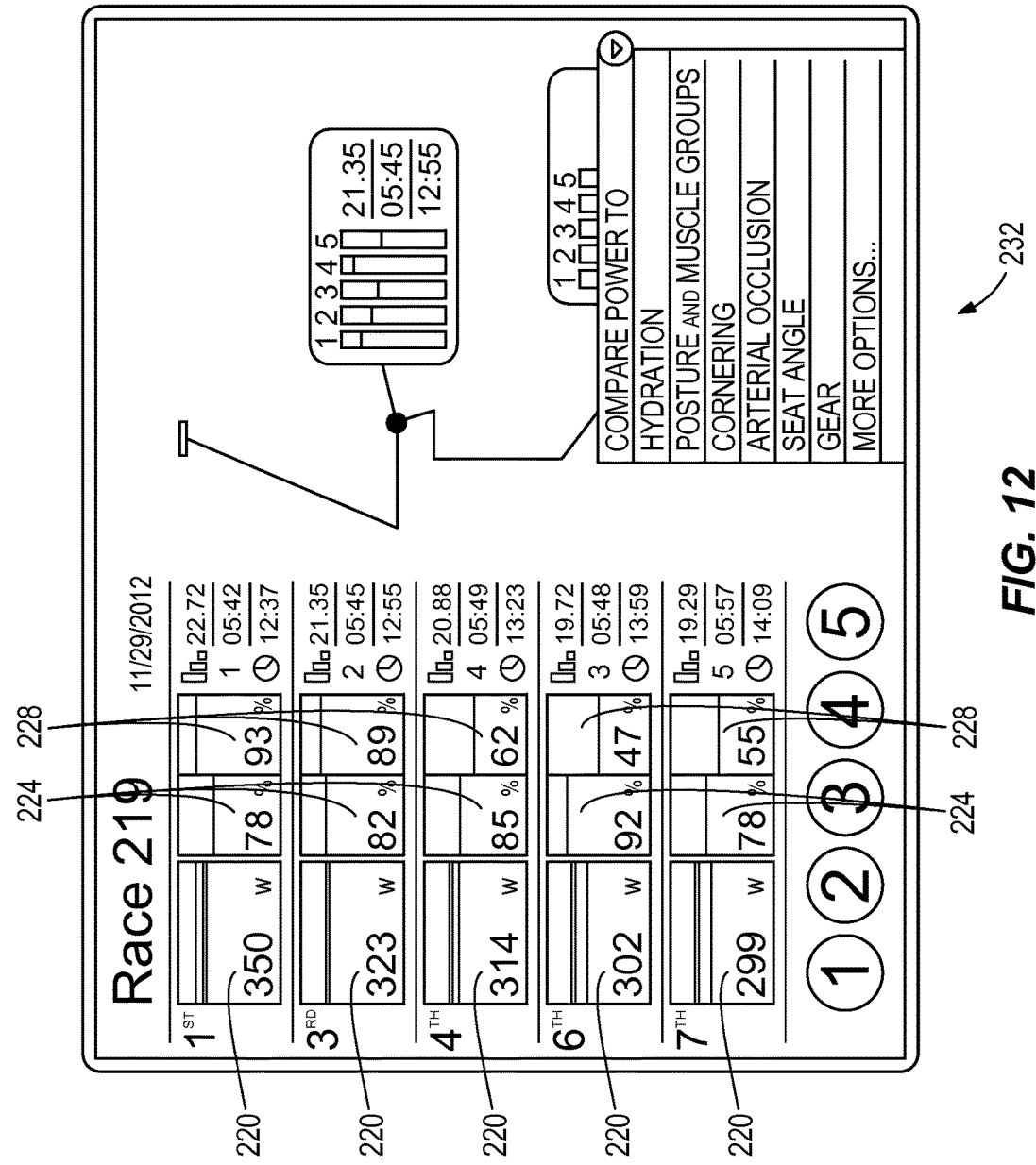
FIG. 12. Plane view similar to FIG. 11, illustrating the display device generating a diagnostics display of various physiological parameters.

Referring also to FIG. 11, the signal processor 108 may be configured to generate a comparison of the measured signal with a network of cyclists substantially in real time, and the display device 112 may generate a diagnostics display 216 listing physiological parameters in comparison with the network of cyclists. In the illustrated embodiment, the diagnostics display 216 comprises a listing of wattage output 220, hydration 224, and arterial pressure or force 228, all in comparison with the network of cyclists. In other embodiments, the diagnostics display 216 may comprise a listing of at least one of arterial pressure or force, lung capacity, weight, wattage output, spine alignment, posture, respiratory rate, perspiration rate, heart rate, muscle group use, pedaling cadence, and hydration, all in comparison with the network of cyclists. In still other embodiments, the diagnostics display 216 may comprise a listing of at least one environmental parameter, such as temperature, humidity, air pressure, bank/camber of the bicycle B, traffic signals, dangerous intersections, and race/track history. Referring also to FIG. 12, the display device 216 may generate a diagnostics display 232 of various physiological parameters such as wattage output 220, hydration 224, and arterial pressure or force 228, all in comparison with the network of cyclists in a group race.

3. Method of Monitoring a Physiological Parameter of a Cyclist

The present disclosure is also directed to a method of using the systems 100, 200 to monitor a physiological parameter of the cyclist C. The method comprises measuring a signal representative of the physiological parameter during pedaling. The physiological parameters may comprise at least one of arterial pressure or force, lung capacity, weight, wattage output, spine alignment, posture, respiratory rate, perspiration rate, heart rate, muscle group use, pedaling cadence, and hydration. In some embodiments, the signal is measured from at least one of a crotch portion, a sole portion, a palm portion, a forearm portion, and a torso rib portion of the cyclist C. In other embodiments, the signal may be measured from any other desired locations suitable to monitor a dynamic pressure or force while the cyclist C is pedaling or moving. In some embodiments, the signal is measured at predetermined intervals.

The measured signal is processed with the signal processor 108 to determine a diagnosis. The alert is generated substantially in real time in response to the diagnosis. In some embodiments, the alert may comprise the diagnostics display 128, 216, 232 listing at least one physiological parameter, such as arterial pressure or force, lung capacity, weight, wattage output, spine alignment, posture, respiratory rate, perspiration rate, heart rate, muscle group use, pedaling cadence, and hydration. In further embodiments, the alert may comprise the diagnostics display 216, 232 listing at least one environmental parameter, such as temperature, humidity, air pressure, bank/camber of the bicycle B, traffic signals, dangerous intersections, and race/track history. In some embodiments, a comparison of the measured signal with a network of cyclists may be generated substantially in real time. The diagnostics display may be positioned anywhere. For example, the diagnostics display may be in the form of a wrist watch, a computer, a mobile phone, or a television.

The foregoing has been provided for illustrative purposes only and is not intended to limit the scope of the invention as set forth in the claims.

What is claimed is:
1. A system for monitoring a physiological parameter of a cyclist, comprising:
 a garment configured to be worn by the cyclist;
 a plurality of sensors including one or more sensors fixedly coupled to a crotch portion of the garment and configured to measure a perineal arterial occlusion force;
 a signal processor operatively coupled to the sensor, wherein the signal processor is configured to receive a signal from one or more sensors of the plurality of sensors, the signal indicative of the measured perineal arterial occlusion force, receive a user-selected perineal arterial occlusion force level, and generate an alert in response to the measured perineal arterial occlusion force;

wherein the garment is configured to position the one or more sensors fixedly coupled to the crotch portion of the garment proximate the left and right pudendal arteries of the cyclist when the garment is worn by the cyclist; and wherein the signal processor is configured to generate the alert based on a comparison of the measured perineal arterial occlusion force and a user-selected perineal arterial occlusion force level.

2. The system of claim 1 further comprising a data storage operatively coupled to the sensor and configured to record the signal.

3. The system of claim 1 further comprising a display device operatively coupled to the signal processor and configured to generate a display in response to the signal substantially in real time.

4. The system of claim 3, wherein the display device is coupled to a handlebar of a bicycle.

5. The system of claim 3, wherein the display comprises a listing of one or more parameters selected from a group consisting of arterial force, lung capacity, weight, wattage output, spine alignment, posture, respiratory rate, perspiration rate, heart rate, muscle group use, and hydration.

6. The system of claim 1, wherein the one or more sensors are configured to generate the signal indicative of the measured perineal arterial force at predetermined intervals.

7. The system of claim 1 further comprising a signal transmission network operatively coupled to the plurality of sensors and the signal processor and configured to transmit the signal indicative of the measured perineal arterial occlusion force according to at least one network interface selected from a group consisting of a wired interface and a wireless interface.

8. The system of claim 1, wherein each of the plurality of sensors is one of a pressure sensor and a force sensor.

9. The system of claim 1, wherein the signal processor is configured to generate a comparison of the measured signal with a network of cyclists substantially in real time.

10. The system of claim 1, further comprising one or more straps each coupled to an additional sensor of the plurality of sensors, and wherein adjusting the straps re-positions the additional sensor with respect to the garment.

11. The system of claim 1, further comprising one or more straps each coupled to an additional sensor of the plurality of sensors, and wherein adjusting the straps re-positions the additional sensor with respect to the cyclist when the garment is worn by the cyclist.

12. The system of claim 1, wherein at least one additional sensor of the plurality of sensors is coupled to the garment by at least one fastener selected from a group consisting of hook-and-loop fasteners and adhesive tape.

13. The system of claim 1, wherein the plurality of sensors includes a sensor configured to monitor respiratory rate.

14. The system of claim 1, wherein the signal processor is configured to generate the alert based on the comparison of the measured perineal arterial occlusion force and the user-selected perineal arterial occlusion force level by generating the alert when the measured perineal arterial occlusion force exceeds a predetermined percentage of the user-selected perineal arterial occlusion force level.

15. The system of claim 1, wherein the signal processor is configured to receive the user-selected perineal arterial occlusion force level by receiving a user-selected percentage, and wherein the signal processor is configured to generate the alert based on the comparison of the measured perineal arterial occlusion force and the user-selected perineal arterial occlusion force level by generating the alert when the measured perineal arterial occlusion force exceeds the user-selected percentage of a predetermined perineal arterial occlusion force level.

16. The system of claim 1, wherein the plurality of sensors are further configured to measure at least one additional parameter selected from a group consisting of weight, heart rate, blood pressure, and a combination thereof.

17. The system of claim 1, wherein the plurality of sensors are further configured to measure a cadence of the cyclist, and wherein the signal processor is configured to monitor the signal indicative of the measured perineal arterial occlusion force at a data acquisition frequency defined at least in part by the measured cadence of the cyclist.

* * * * *